United States Patent [19]
Halawani

[11] Patent Number: 5,557,033
[45] Date of Patent: Sep. 17, 1996

[54] METHOD OF INCREASING EGG PRODUCTION IN AVIAN SPECIES BY ACTIVE IMMUNIZATION AGAINST VASOACTIVE INTESTINAL PEPTIDE

[75] Inventor: Mohamed E. Halawani, Shoreview, Minn.

[73] Assignee: Regents of the University of Minnesota, Minneapolis, Minn.

[21] Appl. No.: 949,797

[22] Filed: Sep. 22, 1992

[51] Int. Cl.$^6$ ............................ C12N 15/00; A61K 39/00
[52] U.S. Cl. ...................... 800/2; 424/185.1; 424/198.1; 800/DIG. 4; 800/DIG. 5
[58] Field of Search ............................... 800/2; 424/185.1, 424/198.1

[56] References Cited

FOREIGN PATENT DOCUMENTS 9108220  6/1991  WIPO .

OTHER PUBLICATIONS

M. E. El Halawani et al., "Vasoactive intestinal peptide is a hypothalamic prolactin–releasing neuropeptide in the turkey (*Meleagris gallopavi*)," *Gen. Comp. Endocrinol.*, 78, 66–73 (1990).

M. E. El Halawani et al., "Enhanced vasoactive intestinal peptide–induced prolactin secretion from anterior pituitary cell of incubating turkeys (*Meleagris Galloparvo*)," *Gen. Comp. Endocrinol.*, 80, 138–145 (1990).

T. R. Knapp et al., "Gonadal steroid modulation of basal and vasoactive intestinal polypeptide–stimulated prolactin release by turkey anterior pituitary cells," *Gen. Comp. Endocrinol.*, 72, 226–236 (1988).

R. W. Lea et al., "Passive immunization against chicken vasoactive intestinal polypeptide suppresses plasma prolactin and crop sac development in incubating ring doves," *Hormones Behav.*, 25, 283–294 (1991).

L. J. Mauro et al., "Alterations in hypothalamic vasoactive intestinal peptide–like immunoreactivity are associated with reproduction and prolactin release in female turkey," *Endocrinol.*, 125, 1795–1804 (1989).

G. R. Pitts et al., "The effect of vasoactive intestinal polypeptide perfused into the median eminence on plasma prolactin, pituitary prolactin content, and prolactin mRNA in laying turkeys," *Poultry Sci.*, 71, p. 21, Abstract No. 61 (1992).

I. Rozenboim et al., "The effect of ovine prolactin (oPRL) administration on hypothalamic vasoactive intestinal peptide (VIP) and anterior pituitary VIP receptors in laying turkey hens,"*Poultry Sci.*, 71, p. 21, Abstract No. 63 (1992).

P. J. Sharp et al., "Relationships between prolactin, LH and broody behavior in bantam hens," *J. Endocrinol.*, 118, 279–286 (Aug. 1988).

M. Xu et al., "Effect of selective drugs for dopaminergic $D_1$ and $D_2$ receptors on cVIP–induced PRL mRNA in turkey hens,"*Poultry Sci.* 71, p. 21, Abstract No. 62 (1992).

T. R. Knapp el al. "General Steroid Modulation of Basal and Vasoactive Intestinal Polypeptide–Stimulated Proactin Release By Turkey Anterior Pituitary Cells." May 11, 1988, pp. 226–236.

P. J. Sharp et al. "The Role of Hypothalamic Vasoactive Intestinal Polypeptide in the Maintenance of Prolactin Secretion in Incubating Bantam Hens: Observations Using Passive Immunization, Radio–immunoassay and Immunohistochemistry." Dec. 2, 1988, pp. 5–14.

L. J. Mauro et al. "Alterations in Hypothalamic Vasoactive Intestinal Peptide–like Immunoreactivity Are Associated with Reproduction and Prolactin Release in the Female Turkey," Apr. 27, 1989. pp. 1795–1804.

M. E. El Halawani et al. "Vasoactive Intestinal Peptide is a Hypothalamic Prolactin–Releasing Neuropeptide in the Turkey (Meleagris galloparo)." Jun. 29, 1989. pp. 66–73.

M. E. Halawani et al. "Ehanced Vasoactive Intestinal Peptide Induced Prolactin Secretion from Anterior Pituitary Cells of Incubating Turkeys (*Melagris galloparo*)." Oct. 23, 1989. pp. 138–145.

R. W. Lea et al. "Passive Immunization Against Chicken Vasoactive Intestinal Polypeptide Suppressed Plasma Prolactin and Crop Sae Development in Incubating Ring Doves." 1991. pp. 283–294.

El Halawani et al. "Increased egg production by active immunization against vasoactive intestinal peptide in the turkey," Poultry Science vol. 1 SUPP, 1993, p. 94.

El Halawani et al. "Regulation of prolactin and its role in Gallinaceous bird reproduction."J. Experim. Zoology. Dec. 1984.

Talbot et al. "Pituitary prolactin messenger ribonucleic acid levels in incubating and laying hens: effects of manipulating plasma levels of vasoactive intestinal polypeptide." Endocrinology, Jul. 1991.

WO, A, 91 08220 (Houen G. et al.) 13 Jun. 1991.
Yajoma et al Chem. Pharm. Bul. 27(12): 3199, 1979.
Halawani et al. J. Exp. Zool. 232: 521, 1984.
Halawani et al. Poul. Sci. 72(Surrel): 94, 281, 1993.
Shays et al. J. Endocrinol. 122: 5, 1989.
Talbot et al. Endocrinol 129(1): 496, 1991.

*Primary Examiner*—Suzanne E. Ziska
*Attorney, Agent, or Firm*—Schwegman, Lundberg, Woessner & Kluth, P.A.

[57] ABSTRACT

The present method of increasing egg production in laying turkey hens includes actively immunizing the hens with vasoactive intestinal peptide. The peptide is conjugated to a protein to induce an antibody response in the hens. The resulting antibodies tie up vasoactive intestinal peptide naturally produced in the turkey. This lack of naturally produced VIP in the turkey in turn prevents the secretion of the hormone prolactin from the pituitary gland of the hens to eliminate the onset of broody behavior. The hens are immunized prior to the laying season and subsequently boosted with immunizations approximately once per month during the laying season.

8 Claims, 3 Drawing Sheets

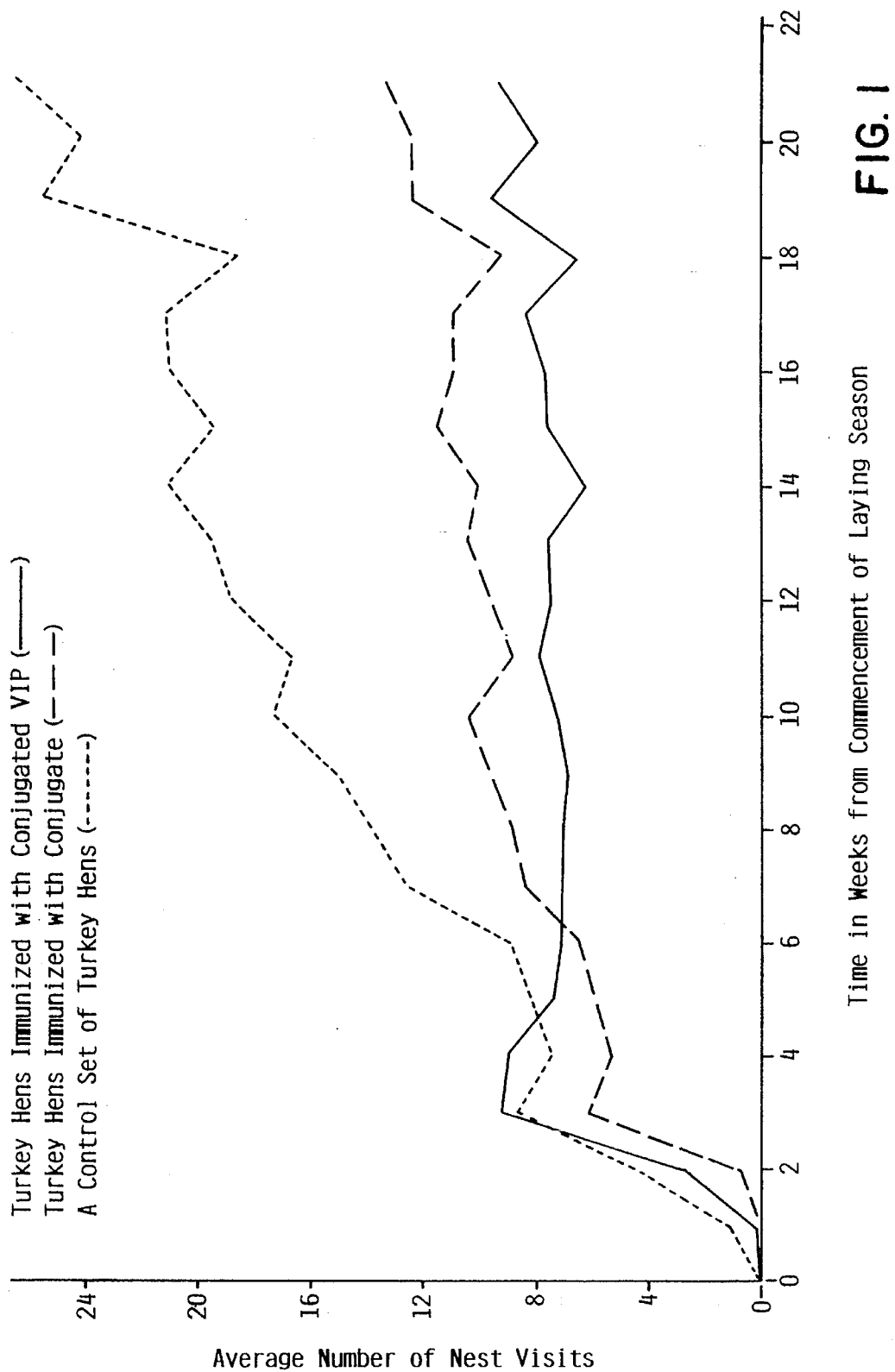

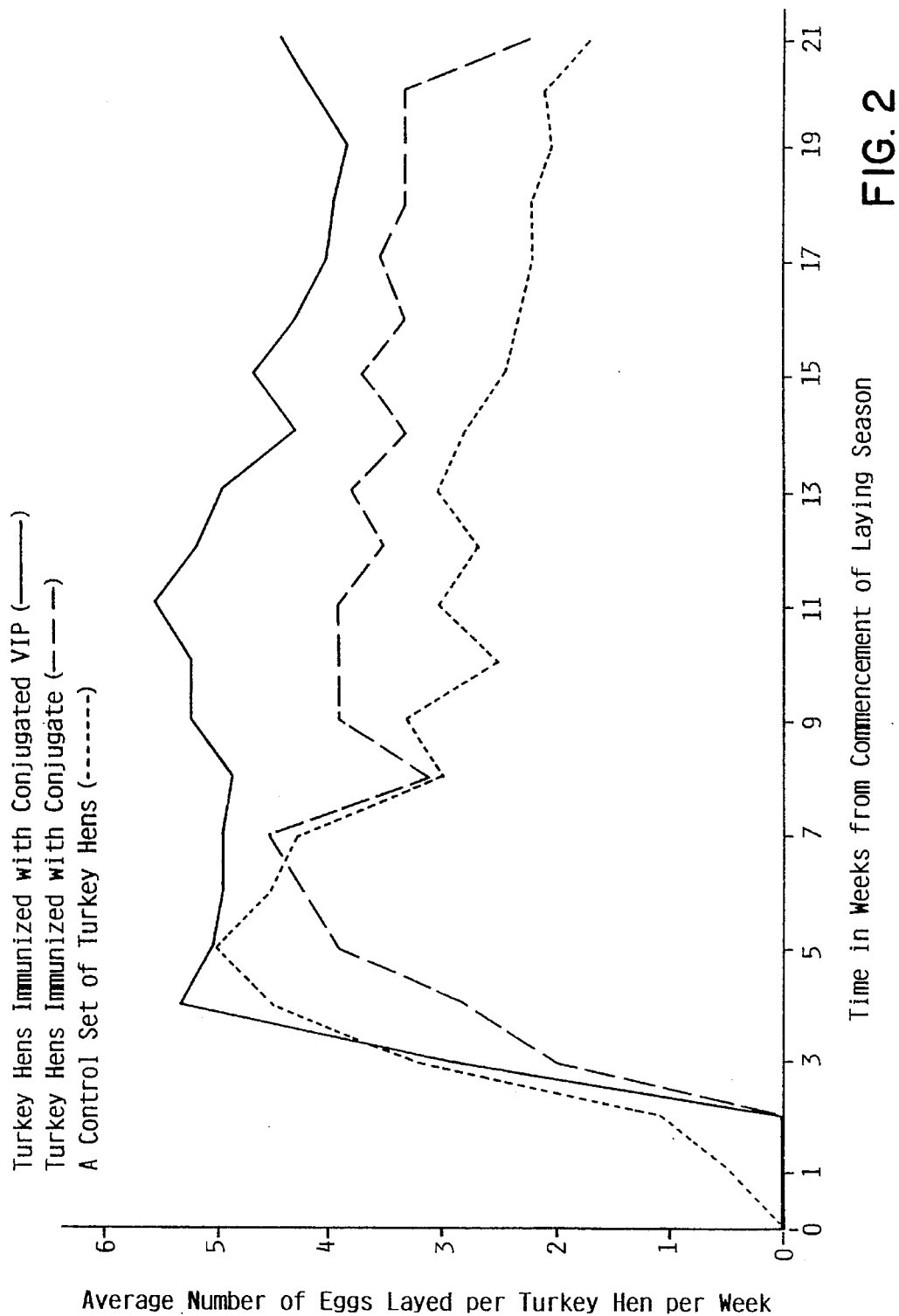

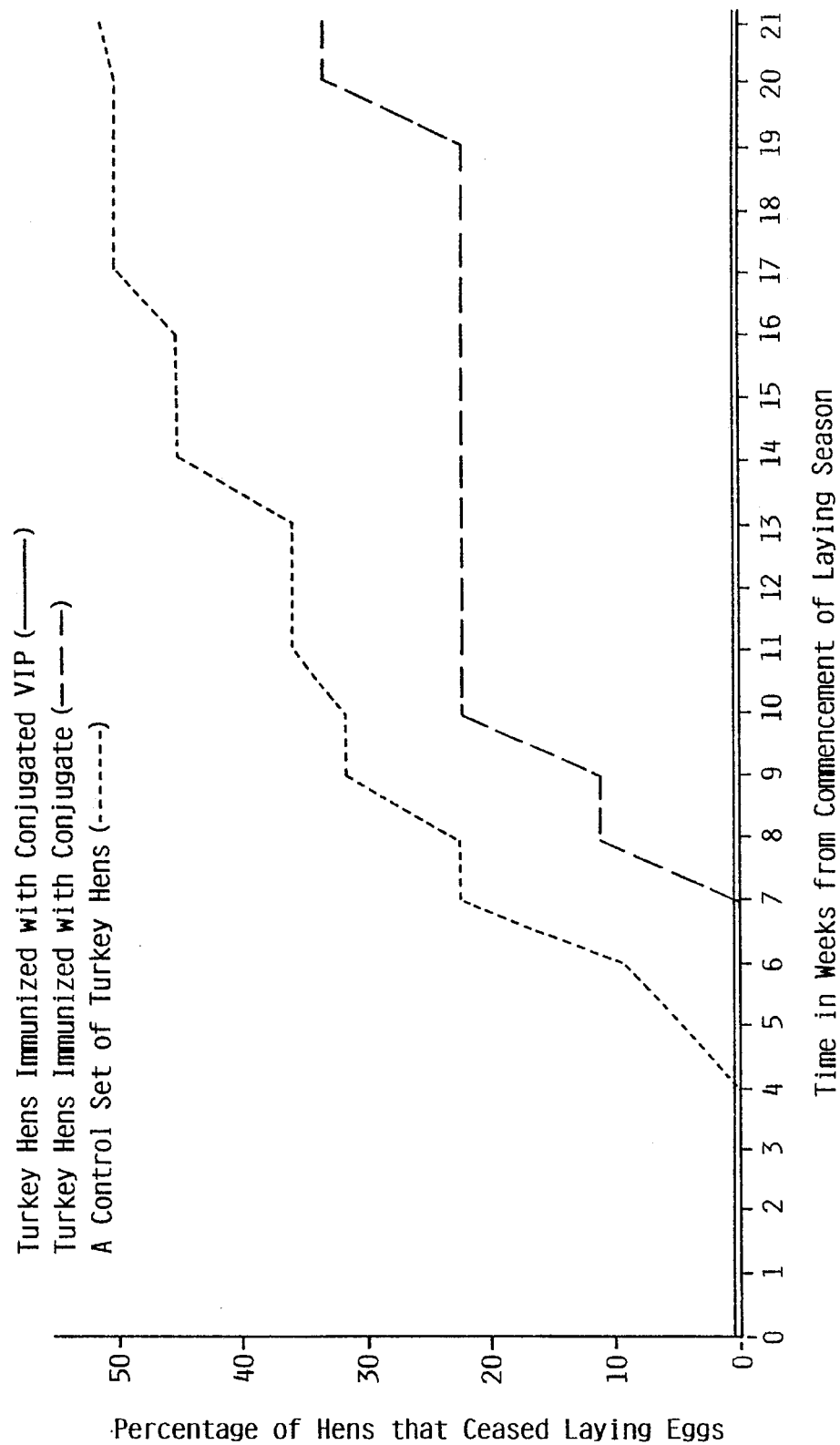

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 28 amino acids
        ( B ) TYPE: amino acid
        ( D ) TOPOLOGY: unknown to applicant ( x i ) SEQUENCE DESCRIPTION: SEQ ID NO: 1:

```
His Ser Asp Ala Val Phe Thr Asp Asn Tyr
 1               5                  10
Ser Arg Phe Arg Lys Gln Met Ala Val Lys
                15                  20
Lys Tyr Leu Asn Ser Val Leu Thr
                25
```

METHOD OF INCREASING EGG PRODUCTION IN AVIAN SPECIES BY ACTIVE IMMUNIZATION AGAINST VASOACTIVE INTESTINAL PEPTIDE

BACKGROUND OF THE INVENTION

The present invention relates to a method of increasing egg production in turkeys and other Avian species and, more particularity, to carrying out such a method with active immunization against vasoactive intestinal peptide.

Turkeys are selected mainly for body size instead of reproductive performance, which declines with an increase in body size. As a result, reproductive efficiency of turkeys is low. Turkey hens generally lay about 73–110 eggs per hen over a 30-week production period or "season".

Egg production may also be influenced by the general management of breeder flocks and the ability of farm managers to identify and treat broody hens. A broody hen may be described as a hen which has the tendency to nest or incubate their eggs after 10–15 eggs are laid and terminates egg laying activities. Broody turkeys seldom start laying again even after their broodiness has been terminated. Broody behavior is undesirable in the turkey industry because it results in a decreased number of young turkeys hatched per hen.

SUMMARY OF THE INVENTION

An object of the present invention is to increase the egg production of a turkey hen and other Avian species.

A feature of the present invention is the active immunization of turkey hens with a vasoactive intestinal peptide to increase egg production.

Another feature is the conjugation of vasoactive intestinal peptide to a protein to induce a natural antibody response in the turkey.

Another feature is the increase of the antiserum titer by boosting approximately once per month during the laying season.

Another feature of the present method of increasing egg production is the active immunization of turkey hens prior to or simultaneously with the onset of an egg laying season to maintain egg production throughout the season.

Another feature is that the immunization is introduced into the hens with a syringe inserted under the skin on the neck.

An advantage of the present invention is the increase in the number of eggs produced by a turkey.

Another advantage is the increase in the number of eggs produced by a turkey as the laying season draws to a close.

Another advantage of the present method is that the turkey hens are actively immunized. In other words, the turkey hens naturally produce their own antibodies when immunized. In contrast., passive immunization involves generating the antibodies in another species and then transferring such antibodies to the host. These antibodies are typically short-lived in the host and hence require a relatively great number of injections, perhaps as often as on a daily basis to be effective. Passive immunization is self-defeating in that the host typically generates its own antibodies against the injected antibodies, which of course decreases the effectiveness of the injected antibodies.

Another advantage is that the amount of peptide injected into a turkey hen is relatively small.

Another advantage is that the vasoactive intestinal peptide immunization causes no detectable side effects.

Another advantage is that the turkey hens may be immunized only once per laying season. A related advantage is that even if boosters are desired, the boosters may be given no more frequently than once per month. This may be described as chronic active immunization.

BRIEF DESCRIPTION OF THE DRAWINGS

FIG. 1 is a graph depicting nesting behavior (number of nest visits per week) of three groups of turkey hens, namely, turkey hens immunized with chicken vasoactive intestinal peptide conjugated to the protein keyhole limpet hemocyanin, turkey hens immunized with only keyhole limpet hemocyanin and a control group of turkey hens.

FIG. 2 is a graph depicting the egg production in the three groups of turkey hens described relative to FIG. 1.

FIG. 3 is a graph depicting the percentage of hens described relative to FIG.. 1 which ceased laying eggs.

DETAILED DESCRIPTION

The present method for increasing the egg production of turkey hens includes active immunization of the turkey hens with vasoactive intestinal peptide (VIP) conjugated to a protein to produce an antibody response in the turkey hens against the turkey hen's naturally produced VIP. Although the bio-mechanical mechanism is not fully understood, it is believed that the antibodies so produced tie up the turkey hen's naturally produced VIP. This naturally produced VIP, a brain peptide, regulates the secretion of the hormone prolactin from the pituitary gland of the turkey hen. Increased prolactin secretion causes broodiness in turkey hens. Broodiness, in turn, is one of the factors which may lead to poor egg production. Accordingly, egg production is enhanced by binding the turkey hen's naturally produced VIP with the natural antibodies generated by the turkey before the turkey's VIP can act upon the turkey's pituitary gland to increase prolactin secretion.

Three sets of turkey hens were studied. One set of turkey hens was immunized with VIP conjugated to a protein. The second set of turkey hens was immunized with a conjugated protein alone (i.e. a placebo). The third set of turkey hens, a control group, was not immunized.

The first set of turkey hens was immunized with chemically synthesized chicken vasoactive intestinal octacosapeptide. This vasoactive intestinal octacosapeptide is produced naturally in chickens and may be referred to as chicken VIP or cVIP. This particular VIP has the amino acid chain of His-Ser-Asp-Ala-Val-Phe-Thr-Asp-Asn-Tyr-Ser-Arg -Phe-Arg-Lys-Gln-Met-Ala-Val-Lys-Lys-Tyr-Leu-Asn-Ser-Val-Leu -Thr-$NH_2$. cVIP is cross-reactive with any bird of the Avian species, including turkeys and ducks. In other words, turkeys and ducks recognize cVIP. It is believed that turkey VIP has not yet been identified.

Since cVIP introduced alone into turkey hens produces only a weak antibody response, it is conjugated to a protein before being introduced into the turkey hen. Such a larger compound produces the desired antibody response. In the case at hand, cVIP was conjugated to keyhole limpet hemocyanin (KLH) to obtain a VIP antiserum for introducing into the turkey hen. Other proteins to which cVIP may be linked to produce such an antibody response include albumin, such as bovine serum albumin.

Chemically synthesized chicken VIP, and chicken VIP conjugated to KLH (i.e. VIP antiserum) are available from Peninsula Laboratories, Inc. of Thousand Oaks, Calif. Since this VIP is chemically synthesized, it is prohibitively expensive for use on a large scale in the turkey industry. However, turkey VIP may be conjugated to a protein such as KLH to produce an antibody response. Turkey VIP may be generated on a mass scale by cloning the turkey vasoactive intestinal peptide gene, and producing recombinant turkey vasoactive intestinal peptide.

To determine whether the antibodies produced by the VIP immunization in fact bind to VIP such as by forming complexes therewith, serum from some of the VIP immunized hens was drawn and mixed with vip labeled with radioactive iodine. An analysis of the mixture revealed that vip binds to the antibodies of the drawn serum. Accordingly, it was concluded that turkey VIP also binds to such antibodies and hence is unable to act upon the pituitary gland to affect an increase in the secretion of prolactin.

To test whether prolactin was being released by the VIP immunized turkeys, VIP immunized turkeys were electrically stimulated on the hypothalamus. It is known that such electrical stimulation causes prolactin release in nonimmunized turkeys. Here, when the VIP immunized turkeys were so stimulated, no prolactin release was observed.

Each of the turkey hens of the first set was immunized with 2.0 ml of cVIP at a concentration of 125 ug on day 1 of week 1. These immunizations were then boosted at 3, 7, 11, and 15 weeks with immunizations of 2.0 ml of cVIP at a concentration of 25 ug.

Each of the turkey hens of the second set was immunized with 2.0 ml of KLH (i.e. a placebo) at a concentration of 125 ug. The immunizations were performed on day 1 of week 1. These immunizations were then boosted at 3, 7, 11, and 15 weeks with immunizations of 2.0 ml of KLH at a concentration of 25 ug.

The adjuvant or carrier for the injections was the oil-based FREUND's carrier.

The turkey hens of the third set were not immunized. This set is referred to as a control group.

The turkey hens were injected under the skin on the neck. If desired, the turkey hens may be injected under the skin under the wing.

All three sets of turkey hens were maintained in a common room and, accordingly, were subjected to similar if not identical environmental conditions such as light and temperature. The room included a set of pens, with each pen having four nests and 8–9 birds comprised of 2–3 birds from each of the three sets. Each set consisted of 18–24 turkey hens.

All turkeys were of the Nicholas strain about to commence their second laying season. The second laying season was brought about by light stimulation on day 1 of week 1 which was also the day the birds were first immunized. The number of nest visits were recorded on a daily basis. The nests included traps which closed upon entrance by a hen and which were checked six times per day for hens and eggs by a caretaker who released the trapped hens and recorded such information. Each of the turkey hens was identified by a saddle number. A broody hen was defined as a hen which was found trapped in one of the nests at least four times per day and had stopped laying eggs.

As shown in Table I below, which provides the basis for the graph of FIG. 1, the turkey hens which were immunized with the VIP had less of a tendency to turn broody than the birds immunized with the placebo or the birds of the control group. The number of nest visits by turkey hens immunized with the VIP averaged about seven times per week throughout the experiment. In other words, the turkeys immunized with VIP visited the nest about once per day, which is the ideal number of visits, as a turkey typically lays no more than one egg per day. In contrast, the weekly number of nest visits in the control group climbed from about 8 visits in week 5 to over 20 visits by week 21. The weekly number of nest visits by birds immunized with the placebo increased to about 13 visits per week by week 21.

TABLE I

AVERAGE NUMBER OF NEST VISITS PER HEN/WEEK

| Week | Number of nest visits by hens immunized with VIP (SE) | Number of nest visits by hens immunized with Conjugate (SE) | Number of nest visits by hens not immunized (Control) (SE) |
|---|---|---|---|
| 1 | 0.2 (0.19) | 0 (0) | 1.23 (0.44) |
| 2 | 2.73 (1.28) | 0.77 (0.34) | 4.5 (1.19) |
| 3 | 9.33 (2.02) | 6.11 (1.47) | 8.68 (1.33) |
| 4 | 9.06 (1.22) | 5.33 (1.83) | 7.41 (0.72) |
| 5 | 7.4 (0.76) | 6.00 (1.14) | 8.14 (1.12) |
| 6 | 7.13 (0.47) | 6.56 (1.38) | 8.91 (1.55) |
| 7 | 7.00 (0.42) | 8.44 (2.54) | 12.46 (2.02) |
| 8 | 7.00 (0.72) | 8.89 (3.36) | 13.68 (2.60) |
| 9 | 6.87 (0.34) | 9.56 (3.13) | 14.96 (2.58) |
| 10 | 7.27 (0.51) | 10.33 (3.61) | 17.22 (3.18) |
| 11 | 7.87 (0.52) | 8.89 (2.93) | 16.55 (2.8) |
| 12 | 7.47 (0.45) | 9.56 (3.47) | 18.73 (3.4) |
| 13 | 7.60 (0.63) | 10.33 (3.31) | 19.41 (3.24) |
| 14 | 6.20 (0.59) | 10.00 (3.87) | 20.91 (3.5) |
| 15 | 7.47 (0.92) | 11.33 (3.56) | 19.32 (3.59) |
| 16 | 7.67 (0.91) | 10.78 (3.64) | (20.82) (3.57) |
| 17 | 8.27 (2.06) | 10.78 (3.43) | (20.91) (3.59) |
| 18 | 6.53 (1.86) | 9.11 (3.17) | (18.41) (3.15) |
| 19 | 9.53 (2.21) | 12.33 (4.49) | 25.46 (4.09) |
| 20 | 7.93 (1.83) | 12.33 (3.61) | 20.05 (3.19) |
| 21 | 8.87 (1.76) | 13.22 (4.72) | 22.32 (3.69) |

As shown in Table II below, which provides the basis for FIG. 2, the turkey hens which were immunized with VIP laid about 87 eggs per hen over a 19 week product period, which is a 50% increase over the hens of the control group, which laid about 58 eggs per hen over the same period of time. The hens immunized with the placebo alone laid about 65 eggs per hen. During the last week of the experiment, the hens immunized with VIP were laying at the rate of 62.9%. This compares to 31.4% and 24.5% for the hens immunized with placebo alone and the hens of the control group, respectively. In other words, during the last week of the experiment, the VIP immunized hens laid about 150% more eggs than the control group and about 100% more eggs than the group immunized with the placebo.

TABLE II

AVERAGE NUMBER OF EGGS LAID PER TURKEY HEN PER WEEK

| Week | Number of eggs laid by hens immunized with VIP (SE) | Number of eggs laid by hens immunized with Conjugate (SE) | Number of eggs laid by hens not immunized (Control) (SE) |
|---|---|---|---|
| 1 | 0 (–) | 0 (–) | .41 (.21) |
| 2 | 0 (–) | 0 (–) | 1.09 (0.42) |
| 3 | 2.93 (0.27) | 2.00 (0.38) | 3.27 (0.42) |
| 4 | 5.33 (0.26) | 2.78 (1.83) | 4.50 (0.32) |
| 5 | 5.07 (0.22) | 3.89 (1.14) | 5.00 (0.27) |
| 6 | 4.93 (0.27) | 4.22 (1.38) | 4.50 (0.42) |
| 7 | 4.93 (0.34) | 4.56 (2.54) | 4.27 (0.40) |
| 8 | 4.87 (0.72) | 3.11 (3.36) | 3.00 (0.74) |
| 9 | 5.20 (0.34) | 3.89 (3.13) | 3.32 (0.50) |
| 10 | 5.20 (0.51) | 3.89 (3.61) | 2.50 (0.50) |
| 11 | 5.53 (0.52) | 3.89 (2.93) | 3.05 (0.56) |
| 12 | 5.13 (0.45) | 3.56 (3.47) | 2.68 (0.54) |
| 13 | 4.93 (0.63) | 3.78 (3.31) | 3.00 (0.59) |
| 14 | 4.27 (0.59) | 3.33 (3.87) | 2.77 (0.57) |
| 15 | 4.67 (0.92) | 3.67 (3.56) | 2.41 (0.54) |
| 16 | 4.27 (0.33) | 3.33 (0.69) | 2.36 (0.52) |
| 17 | 4.00 (0.34) | 3.56 (0.70) | 2.18 (0.50) |
| 18 | 3.93 (0.44) | 3.33 (0.63) | 2.23 (0.54) |
| 19 | 3.87 (0.46) | 3.33 (0.74) | 2.05 (0.49) |
| 20 | 4.13 (0.34) | 3.33 (0.63) | 2.09 (0.49) |
| 21 | 4.40 (0.39) | 2.22 (0.66) | 1.73 (0.43) |
| TOTAL | 87.60 (3.01) | 65.67 (9.97) | 58.41 (7.06) |

As shown in Table III below, which provides the basis for FIG. 3, all of the turkey hens which were immunized with conjugated VIP continued to lay eggs. None of these turkey hens turned broody. In contrast, 50% of the turkey hens of the control group ceased to lay eggs by week 21. Further in contrast, 33% of the turkey hens immunized with conjugate alone ceased egg production by week 21.

TABLE III

PERCENTAGE OF HENS WHICH CEASED LAYING EGGS

| Week | Percentage of nonlaying hens immunized with VIP (SE) | Percentage of nonlaying hens immunized with Conjugate (SE) | Percentage of nonlaying hens not immunized (Control) (SE) |
|---|---|---|---|
| 1 | 0.0 | 0.0 | 0.0 |
| 2 | 0.0 | 0.0 | 0.0 |
| 3 | 0.0 | 0.0 | 0.0 |
| 4 | 0.0 | 0.0 | 0.0 |
| 5 | 0.0 | 0.0 | 4.5 |
| 6 | 0.0 | 0.0 | 9.1 |
| 7 | 0.0 | 0.0 | 22.7 |
| 8 | 0.0 | 11.0 | 22.7 |
| 9 | 0.0 | 11.0 | 31.8 |
| 10 | 0.0 | 22.0 | 31.8 |
| 11 | 0.0 | 22.0 | 36.3 |
| 12 | 0.0 | 22.0 | 36.3 |
| 13 | 0.0 | 22.0 | 36.3 |
| 14 | 0.0 | 22.0 | 45.5 |
| 15 | 0.0 | 22.0 | 45.5 |
| 16 | 0.0 | 22.0 | 45.5 |
| 17 | 0.0 | 22.0 | 50.0 |
| 18 | 0.0 | 22.0 | 50.0 |
| 19 | 0.0 | 22.0 | 50.0 |
| 20 | 0.0 | 33.0 | 50.0 |
| 21 | 0.0 | 33.0 | 50.9 |

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. A method of increasing egg production in an Avian species, comprising (a) actively immunizing hens of said Avian species with a vasoactive intestinal peptide having SEQ. ID NO: 1 conjugated or linked to an immunogenic protein, wherein said immunization occurs prior to, or simultaneously with, the onset of a laying season: and (b)boosting said immunized hens during the laying season with the peptide conjugated or linked to the immunogenic protein.

2. The method of claim 1, wherein said boosting is approximately once per month during the laying season.

3. A method of increasing egg production of turkey hens having a laying season, comprising actively immunizing the hens with a vasoactive intestinal peptide having SEQ ID NO: 1 conjugated or linked to an immunogenic protein to induce an antibody response in the hens, wherein the hens are immunized with the vasoactive intestinal peptide having SEQ ID NO: 1 conjugated or linked to an immunogenic protein prior to, or simultaneously with, the onset of the laying season, and wherein said hens are boosted with said peptide conjugate approximately once per month during the laying season.

4. A method of increasing egg production in a bird having a laying season, comprising actively immunizing said bird with a vasoactive intestinal peptide having SEQ ID NO: 1 conjugated or linked to an immunogenic protein, said immunizing occurring at about the start of, or prior to, the laying season.

5. A method of increasing egg production in a bird comprising actively immunizing the bird with a vasoactive intestinal peptide having SEQ ID NO: 1 conjugated or linked to an immunogenic peptide, wherein said immunization occurs prior to, or simultaneously with, the onset of the laying season to inhibit prolactin from causing broodiness in the bird.

6. The method of claim 5, wherein said bird is a turkey hen.

7. A turkeyhen actively immunized with a vasoactive intestinal peptide having SEQ ID NO: 1 conjugated or linked to an immunogenic protein, wherein the egg production by the immunized turkey hen is enhanced relative to the egg production of an unimmunized turkey hen and wherein said actively immunized hen produces antibodies to vasoactive intestinal peptide or to said vasoactive intestinal peptide having SEQ ID NO: 1 conjugated or linked to an immunogenic protein.

8. A bird actively immunized with a vasoactive intestinal peptide having SEQ ID NO: 1 conjugated or linked to an immunogenic protein, wherein the egg production by said actively immunized bird is enhanced relative to the egg production of an unimmunized bird and wherein said actively immunized bird produces antibodies to vasoactive intestinal peptide or to said vasoactive intestinal peptide having SEQ ID NO: 1 conjugated or linked to an immunogenic protein.

* * * * *